United States Patent [19]
Chedid et al.

[11] Patent Number: 5,932,208
[45] Date of Patent: *Aug. 3, 1999

[54] COMPOSITIONS AND METHODS FOR THE USE OF SUCH COMPOSITIONS IN HUMAN THERAPEUTICS, CHARACTERIZED BY THE ASSOCIATION OF A MURAMYL PEPTIDE WITH A CYTOKINE

[75] Inventors: Louis Chedid, Paris; Georges Bahr, Puteaux; Pierre Lefrancier, Gif sur Yvette, all of France

[73] Assignee: Vacsyn S.A., Paris, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/522,342

[22] PCT Filed: Mar. 21, 1994

[86] PCT No.: PCT/FR94/00307

§ 371 Date: Nov. 13, 1995

§ 102(e) Date: Nov. 13, 1995

[87] PCT Pub. No.: WO94/21275

PCT Pub. Date: Sep. 29, 1994

[30] Foreign Application Priority Data

Mar. 19, 1993 [FR] France ................................... 93 03230
Mar. 31, 1993 [FR] France ................................... 93 03787

[51] Int. Cl.$^6$ .......................... A61K 45/05; A61K 38/21; A01N 61/00; C07K 1/00
[52] U.S. Cl. ....................... 424/85.1; 424/85.2; 424/85.4; 514/1; 514/2; 530/350
[58] Field of Search ............................ 514/1, 2; 530/350; 424/85.1, 85.2, 85.4

[56] References Cited

FOREIGN PATENT DOCUMENTS 0 228833  7/1987  European Pat. Off. .
0 257890  3/1988  European Pat. Off. .
0 329609  8/1989  European Pat. Off. .

OTHER PUBLICATIONS

Chemical Abstracts 115:222927q (1991).
Chemical Abstracts 112:229333q (1990).
Chemical Abstracts 112:176682u (1990).
Chemical Abstracts 118:73306u (1993).
Malik et al., Br. J. Cancer, 63, 399–403 (1991).
Wyde et al., J. Bio. Response Modifiers, 9, 98–102 (1990).
Azuma et al., Adv. Exper. Med. & Biology, 319, 253–263 (1992).
Pouillart et al., J. Interferon Research, 11, p. S162 (1991).
Pouillart et al., J. Interferon Research, 11, p. S257 (1991).
Sanceau et al., Immunology, 69, 52–56 (1990).

Primary Examiner—Ardin H. Marschel
Assistant Examiner—Jezia Riley
Attorney, Agent, or Firm—Birch, Stewart, Kolasch and Birch, LLP

[57] ABSTRACT

A therapeutical composition for use in humans, comprising a combination of at least one natural or recombinant and preferably human cytokine with at least one muramyl peptide selected from those which, when administered in vivo together with an interferon, also induce an increased in vivo production of an interleukin-1 receptor antagonist IL-1 RA, but preferably do not induce any increase in TNF, IL-8 and IL-1 cytokines. Said composition is useful for antiviral and antitumoral therapies and/or for promoting restoration of the haematopoietic system, particularly in individuals with a weakened immune system.

30 Claims, No Drawings

COMPOSITIONS AND METHODS FOR THE USE OF SUCH COMPOSITIONS IN HUMAN THERAPEUTICS, CHARACTERIZED BY THE ASSOCIATION OF A MURAMYL PEPTIDE WITH A CYTOKINE

Interferons (more especially α-interferon) are secreted by leucocytes. They are therefore classed as cytokines, which are mediators produced principally by the cells of the immune system. In general, cytokines may be regarded as hormones characteristic of the immune system. The possibility of producing cytokines by genetic recombination has opened up the way to more detailed studies of the behaviour of some of these cytokines, especially recombinant interferons in animals. Of the interferons, the one which has been studied the most is α-interferon (α-IFN) which is subdivided into α-IFN 2a, α-IFN 2b and α-IFN 2c.

In particular, the antiviral activity of some murine interferons, and even the potentiation of this activity in mice by some derivatives of N-acetyl-muramyl-L-alanyl-D-isoglutamine (MDP) or homologues thereof, have already been demonstrated. On the other hand, as indicated by F. Dianzani in his article entitled "Interferon Treatments: how to use an Endogenous System as a Therapeutic Agent" in the Journal of Interferon Research, Special Issue, May 1992, Mary Ann Liebert, Inc., Publishers, pp. 109–118, the large number of clinical trials carried out on humans with interferons have been "more than disappointing". Although animal tests seemed to open up wide therapeutic possibilities, their poorly controlled secondary effects have meant that it has hitherto been possible to use them only in a restricted number of therapeutic indications. Thus, it has hitherto been proposed to use α-IFN 2a only in a reduced number of "niches", as indicated also by "Scrip's Cytokines Report", PJB Publications Ltd. 1993, in respect of the difficulties encountered in the use of interferons in human therapeutics:

a) in the treatment of the most serious cases of hepatites B and C. The treatments consist in daily administrations or administration at the rate of three times per week of from 5 to 10 million units for from 3 to 6 months. Positive results are observed in from 30 to 40% of cases;

b) in the field of cancer, the treatment of hairy cell leukaemia and chronic myelogenic leukaemia, the uses envisaged are AIDS, Kaposi's syndrome, multiple myeloma, melanoma and certain types of carcinoma.

The serious nature of these syndromes is such that it has also led to the acceptance of the serious secondary effects accompanying the use of α-IFN in human therapeutics. 98% of patients thus treated suffer from an influenza syndrome, which is often extremely severe, accompanied by nausea, vomiting, disorders of the central and peripheral nervous system and cardiac disorders. These effects are attributed at least in part to the induction by interferon of pyretic mediators which could be IL-1 and prostaglandins, the production of which would be activated by interferon. Added to this are bouts of tiredness, anorexia and weight loss, which could be linked at least in part with the production of TNF and/or the increased expression of TNF receptors which are also induced by interferons. Any procedure which optimised the beneficial effects of interferons or cytokines that can be used therapeutically while at the same time optimising the production of, or the activity of, cytokines or other undesirable biological mediators, such as IL-1, IL-8 and/or TNF (Tumour Necrosis Factor) would be doomed to certain failure.

Finally, the administration of interferons is often accompanied by severe leucopenia and thrombopenia accompanied by a blockage of the maturation of myeloidal precursors. These phenomena make it necessary to interrupt the interferon-based treatments periodically in order to authorise a regeneration of the blood formula each time.

All these disadvantages have hitherto prevented any exploration of the real possibilities of using interferons in human therapeutics, except for the treatment of the few syndromes mentioned above.

Similar difficulties are encountered with other cytokines, the therapeutic value of which would be undisputed if it were possible to overcome these difficulties. This would apply, for example, to IL-2, IL-3, IL-6, G-CSF, M-CSF, GM-CSF, etc . . . TNF and IL-1, the therapeutic possibilities of which can be exploited only rarely.

It is known that it has been proposed to use, in particular, IL-3 and some CSFs to accelerate haematopoietic recovery in patients affected by marrow aplasia (which is manifested under the effect of an endogenous and/or iatrogenous pathogenic factor), in particular at the end of chemotherapeutic treatments or in patients who have undergone marrow transplants. However, the use of IL-3 in human therapeutics or of the most active CSFs (for example GM-CSF) in practice comes up against the same difficulties as does α-interferon.

Added to these therapeutic disadvantages is the excessive cost of current treatments based on therapeutically useful cytokines. The doses administered, in as much as it is possible to regulate the effect thereof in vivo, are considerable compared with therapeutically useful doses, which can perhaps be explained by the fact that, unlike-endocrine hormones, cytokines do not act at a distance but only on the cells close to the secretory cells. In other words, any cytokine administered which does not reach the target cells may be regarded as "therapeutically lost".

The aim of the invention is to overcome at least the majority of these disadvantages and difficulties.

The possibility of benefiting from the therapeutic effects of α-IFN or of therapeutically useful cytokines other than α-IFN, where appropriate in more reduced doses, without causing unacceptable secondary effects would be a very important step both therapeutically and economically. This is one of the objectives of the invention.

More specifically, the aim of the invention is to increase the efficacy of therapeutic treatments that use an interferon or, more generally, a cytokine having a therapeutic value, and even to widen the therapeutic fields of these cytokines (including, of course, interferon), while at the same time overcoming the majority of the disadvantages mentioned above, more especially in relation to interferons.

The invention is largely based on the finding that the association of some muramyl peptides with a cytokine that can exhibit a therapeutic effect in humans has henceforth made it possible to use some of those cytokines in human therapeutics at effective doses, which could not be seriously contemplated previously, and in the most suitable cases (for example the case of interferon) opening up the way to ranges of therapeutic treatment for clinical indications which are considerably greater in number and efficacy. It has been found that these muramyl peptides also permitted the induction of the in vivo synthesis of other cytokines which do not appear, at least in detectable amounts, after the administration of only one of the two elements, interferon and muramyl peptide, which means that the therapeutic activity spectra of cytokines and muramyl peptides is broadened. Of the cytokines induced, there may be mentioned more especially interleukin 6 (IL-6), G-CSF and an interleukin 1 receptor antagonist (IL-1 RA). What is more, the associated administration of specific muramyl peptides and α-interferon (α-IFN) permits the production of the desired effects using sub-optimum doses of cytokine, especially α-IFN, owing to the potentiation of the beneficial effects of the cytokine, but without the induction of undesirable cytokines, especially IL-1, TNF or IL-8.

The invention therefore relates more especially to an association of at least one cytokine with at least one muramyl peptide selected from those which, when administered in vivo in association with an interferon, also induce the increased in vivo production of an interleukin 1 receptor antagonist IL-1 RA and, preferably, do not induce an increase in the IL-I, TNF and IL-8 cytokines.

It is preferable to use more especially those muramyl peptides which, in accordance with the above-mentioned conditions, also induce an increased in vivo synthesis of IL-6 or G-CSF, or preferably both, when they are administered with an interferon.

The invention is not limited to the association of an (α, β or γ) interferon with such a muramyl peptide. The interferons may also be replaced by other cytokines, especially by those identified above by way of example. In other words, the invention is derived from the capacity of specific muramyl peptides, when they are administered in association with a cytokine:

- to potentiate the biological activity of the cytokine in question, also permitting the attainment of the desired effects after the administration of lower doses than those currently considered to be therapeutically necessary;
- not to promote and possibly even to inhibit the in vivo induction by that cytokine of the factors limiting its possible therapeutic applications, as was observed in the case of the association with IFN and, where appropriate and simultaneously;
- to induce the in situ production, on the one hand, of inhibitors of these limiting factors, for example IL-1 RA and, especially when the cytokine is an interferon, the soluble TNF receptor (STNF-R) and, on the other hand, the in situ secretion by the competent cells of the lymphoid system of cytokines, for example IL-6 and G-CSF in the case of the interferons, which thus enables the spectrum of action of the cytokine of the administered association to be broadened.

The invention therefore relates to any association which uses one or more cytokines and a muramyl peptide selected on the basis of its capacity not to induce and even to inhibit in humans the secretion by their competent cells of biological mediators, such as IL-1 and/or IL-8 and/or TNF, or at the very least to inhibit the effects thereof. The highly probable role of these mediators in the secondary effects associated with the administration of some cytokines is known. The capacity of muramyl peptide to potentiate the action of the cytokine while at same time protecting the host against the induction of cytokines or other harmful mediators may, in each case, be verified by comparative in vivo tests, preferably in humans, involving, on the one hand, the selected cytokine alone and, on the other hand, an association of that cytokine with the selected muramyl peptide, and the detection and measurement on a comparative basis (for example in RIA or ELISA tests using the appropriate antibodies) of the amounts of the induced cytokines studied. The results which can be obtained are illustrated, of course in non-limiting manner, in the examples which follow which are applied to α-interferon and are explained hereinafter.

The cytokines used are preferably always cytokines of human origin. It should be emphasised that this term is to be understood as covering, in addition to natural cytokines of human origin (the difficulties involved in their isolation in suitable quantities are well known), corresponding recombinant cytokines produced by genetic engineering techniques, that is to say, cytokines which are nevertheless characterised by amino acid sequences identical to those of natural cytokines, which does not, however, exclude equivalent amino acid sequences which differ from the previous ones, especially by substitution, addition or deletion of amino acids entailing neither substantial modification of the characteristic properties of recombinant cytokines having "identical sequences", nor the appearance of harmful properties (for example the induction of antibodies in the human host).

The muramyl peptides used in the invention are preferably muramyl peptides which are selected especially from those which are characterised by the following general formula:

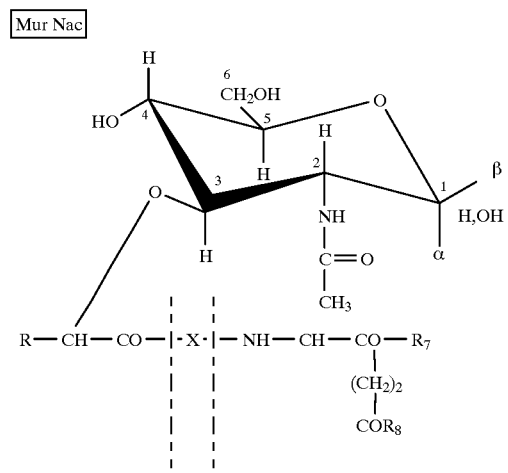

wherein the group R is hydrogen or a methyl group; X is L-alanyl, L-leucyl, L-isoleucyl, L-valyl, L-threonyl, L-(N-methyl)-alanyl and $R_7$ and $R_8$ are independently of one another hydroxy, amino or $O(CH_2)_xH$ groups, wherein x=1, 2, 3, 4 or 5, or peptide groups comprising from 1 to 3 amino acid residues, preferably of laevorotatory nature.

A category of preferred muramyl peptides is that in which:
  $R=CH_3$,
  X is L-alanyl or L-threonyl,
  $R_7$ is an $O(CH_2)_{x'}H$ group, wherein x'=1, 2, 3 or 4,
  $R_8$ is an amino group or an $O(CH_2)_{x''}H$ group, wherein x''=1, 2, 3 or 4.

Especially preferred muramyl peptides are murametide ($R=CH_3$, X=L-Ala, $R_7=OCH_3$ and $R_8=NH_2$, murabutide ($R=CH_3$, X=L-Ala, $R_7=OnC_4H_9$ and $R_8=NH_2$) and finally muradimetide ($R=CH_3$, X=L-Ala, $R_7=R_8=OCH_3$) and, where appropriate, their homologues in which the L-alanyl residue of their peptide group has been replaced by a threonyl group.

It will be appreciated that the above classes of muramyl peptide of hydrophilic nature are in no way limiting. Lipophilic muramyl peptides, such as those described in French patent No. 8407340, may also be used within the scope of the invention.

It will additionally be appreciated that it is also possible to use any other adjuvant muramyl peptides carrying substituents in positions 1, 4 or 6 of the saccharide group, provided they have the same favourable effects as the preferred muramyl peptides mentioned above.

It should also be noted that the term "association" does not mean that the selected cytokine and muramyl peptide are necessarily administered to the human host in admixture or simultaneously. The term extends also to any use or presentation involving their administration at non-zero time intervals, it being understood, however, that these intervals must be sufficiently short to permit the mutual interaction of the two constituents of the association under the conditions indicated above.

This type of association using interleukins and muramyl peptides is efficacious when the interleukins are administered in the following doses:

in the case of interferon:
    from 0.05 MU/kg/day to 10 MU/kg/day, and preferably from 0.5 MU/kg/day to 5 MU/kg/day, an optimum dose being from 1 MU/kg/day to 5 MU/kg/day.

b) that the subjects receiving the association exhibit a significant increase in the number of cells of the white line compared with the group treated with IFN;

c) that there appear, in the plasma of the subjects treated with the association, immunity mediators: interleukin 6, G-CSF, whereas none of the principal pyrogenic and inflammatory mediators, more especially cytokines IL-1, IL-8 and TNF, appears to be induced.

These observations are based more especially on the results of the following tests.

FIRST SERIES OF TESTS: subcutaneous injection of mixtures of α-IFNα-2a interferon with either murabutide or murametide:

Healthy subjects undergo a series of tests in order to demonstrate their ability to be included in the test. They receive subcutaneously the mixtures described in the following table I of murabutide (MUB) or murametide (MUM) with α-interferon 2a (α-IFN).

TABLE I

| A MUB | α-IFN | | | | | |
|---|---|---|---|---|---|---|
| B MUM | $10^5$ U | $3 \times 10^5$ U | $10^6$ U | $3 \times 10^6$ U | $6 \times 10^6$ | O |
| A 35 µg/Kg | A I | A II | A III | A IV | A V | control A35 |
| A 100 µg/Kg | A VI | A VII | A VIII | A IX | A X | control A100 |
| B 35 µg/K | B I | B II | B III | B IV | B V | control B35 |
| B 100 µg/Kg | B VI | B VII | B VIII | B IX | B X | control B100 |
| O | control IFN $10^5$ | control IFN $3 \times 10^5$ | control IFN $10^6$ | control IFN $3 \times 10^6$ | control IFN $6 \times 10^6$ | Placebo |

By way of indication, the specific activity of the IFN used is from 4 to 8 IU/mg of proteins.

in the case of IL-2:
    from 0.3 MU/kg/day to 10 MU/kg/day, preferably between 1 MU/kg/day and 2 MU/kg/day, knowing that the specific activity of IL-2, especially marketed by Cetus under the name Proleukin, is of the order of 10 million IU per mg of proteins.

in the case of GM-CSF, the preferred doses are from 1 to 25 µg/kg and per day and more preferably from 5 to 10 µg/kg and per day.

muramyl peptides, especially murabutide, being administered at doses of the order of from 10 to 350 µg/kg/day and preferably from 50 to 200 µg/kg/day; a dose of 100 µg/kg/day is in all cases associated with sub-optimum or optimum doses of cytokine.

Other features of the invention will also become clear from the non-limiting examples described hereinafter.

In the course of clinical trials carried out on healthy human volunteers, α-IFN 2a (interferon Roferon A dosed at 3 MU/ml and marketed by Roche under the mark ROFERON A) was administered in association with muramyl peptides, especially murametide and murabutide. It was demonstrated:

a) that the secretion of neopterine, which is the recognised biological marker indicating the immunostimulatory activity of IFN, was very greatly increased, following the administration of sub-optimum doses of IFN, associated with doses of murabutide or murametide; the same applies to the IL-1 receptor antagonist (IL-1 RA), the synthesis of which is induced slightly by IFN alone and is considerably increased by the addition of muramyl peptides, thus demonstrating a synergistic activity between IFN and the synthetic immunomodulators; this is also true of the soluble TNF receptor (STNF-R);

The subjects are monitored during the three days following the administration of the IFN and/or the muramyl peptides, and all of the tests and investigations necessary to carry out a phase I test are effected.

The following investigations in particular are carried out:

Haematological analysis with white corpuscle counts at the time of injection and then 6 hours, 12 hours, 24 hours, 36 hours, 60 hours and 72 hours after injection.

Blood samples are taken before injection and 6 hours, 24 hours and 48 hours after injection, in order to collect the serum necessary to carry out the tests for neopterine, interleukin 1, 6 and 8, G-CSF, IL-1 RA and α-TNF.

The leucocyte counts are carried out in a COULTER COUNTER automatic cell counter.

The blood samples for the serum tests are centrifuged at 4° C. and 3000 rpm for 10' immediately after they are taken. The sera are stored at −20° C. The leucocyte counts and the neopterine and cytokine tests are carried out using commercial kits.

RESULTS OF THE INVESTIGATIONS AND TESTS

1) Secondary Effects:

The secondary effects reported in the course of the tests (such as migraine, fever and articular pain) were very slight. In particular, the effects of the influenza syndrome type observed with the high doses of IFN of 3M and 6M units are not increased by the combination with the muramyl peptides although there is a great increase in the biological activity of IFN and the appearance of a modified profile of that activity with synthesis of new biological mediators.

2) Leucocyte counts:

Neutrophils are the cells which are the most affected by leucopenic treatments. It is the reduction in the amount of neutrophils which is responsible for the reduction in the non-specific immune defences in subjects subjected to radiotherapy or to cytotoxic and/or myelotoxic chemotherapy. To make reading easier, only the neutrophil counts made at the time when their variation is at its greatest have been given.

TABLE II

Increase in the number of neutrophils in healthy volunteers after the administration of the muramyl peptide-α-IFN association

| α-IFN administered | Muramyl peptide administered | | No. | Neutrophil count |
|---|---|---|---|---|
| (number of units) | compound | Dose (μg/Kg) | tested | % base line[a] |
| 0 | Murabutide | 100 | 6 | 268 ± 43[b] |
| 0 | Murametide | 100 | 4 | 279 ± 67 |
| $1 \times 10^5$ | — | 0 | 6 | 143 ± 34 |
| $1 \times 10^5$ | Murabutide | 100 | 6 | 265 ± 61 |
| $3 \times 10^5$ | — | 0 | 6 | 292 ± 112 |
| $3 \times 10^5$ | Murabutide | 100 | 6 | 169 ± 47 |
| $1 \times 10^6$ | — | 0 | 6 | 147 ± 42 |
| $1 \times 10^6$ | Murabutide | 100 | 6 | 207 ± 46 |
| $1 \times 10^6$ | Murametide | 100 | 6 | 232 ± 18 |
| $3 \times 10^6$ | — | 0 | 6 | 144 ± 19 |
| $3 \times 10^6$ | Murabutide | 100 | 6 | 252 ± 59 |
| $3 \times 10^6$ | Murametide | 100 | 6 | 255 ± 96 |
| $6 \times 10^6$ | — | 0 | 6 | 191 ± 75 |
| $6 \times 10^6$ | Murabutide | 100 | 6 | 226 ± 74 |
| $6 \times 10^6$ | Murametied | 100 | 6 | 298 ± 71 |

[a]: represents the highest values observed during the 24 hours after administration.
[b]: mean ± standard deviation.

3) Neopterine tests:

The tests are carried out on sera taken at 0, 24 and 48 hours. An RIA (Radio Immuno Assay) kit (Behring Diagnostic, France) is used. The results are expressed in nanomoles/ml, and the normal values vary from 4 to 9 nanomoles/ml.

amount of neopterine to be obtained. Although at the highest dose murabutide administered at 100 μg/kg also enables a significant increase to be obtained, this increase is much lower than that observed with the association.

4) IL-1 receptor antagonist (IL-1 RA) tests:

The tests carried out on the sera of subjects who had received $10^6$ units of α-IFN are indicated in the following table (Table IV) which shows the very strong effect of the association of muramyl peptide and interferon (in this case also British Biotechnology Products Ltd. kit).

TABLE IV

Amount of IL-1 receptor antagonist (IL-1 RA) present in the serum of healthy volunteers, 6 hours after the administration of muramyl peptides and α-IFN.

| α-IFN administered | Muramyl peptide administered | | Amounts of IL-1 RA in the serum |
|---|---|---|---|
| (Number of units) | Compound | dose (μg/Kg) | (Pg/ml)[+] |
| 0 | Murabutide | 100 | 496 ± 326[φ] |
| $3 \times 10^5$ | — | 0 | 258 ± 113 |
| $3 \times 10^5$ | Murabutide | 100 | 10 294 ± 16 554* |
| $1 \times 10^6$ | — | 0 | 2 093 ± 1 278 |
| $1 \times 10^6$ | Murabutide | 100 | 16 093 ± 1 621* |
| $1 \times 10^6$ | Murametide | 100 | 16 204 ± 1 879* |
| $3 \times 10^6$ | — | 0 | 7 332 ± 3 215 |
| $3 \times 10^6$ | Murabutide | 100 | 30 563 ± 23 410* |
| $6 \times 10^6$ | — | 0 | 15 523 ± 6 554 |
| $6 \times 10^6$ | Murabutide | 100 | 66 870 ± 36 554* |

[+]: detected 6 hours after the administration of the compounds, the amounts before administration were all less than 200 pg/ml;
[φ]: mean ± standard deviation in the six volunteers of the same group;
*: amounts substantially different from the amounts induced by α-IFN alone ($p < 0.05$–$p < 0.005$ in the Mann Whitney Rank test)

TABLE III

| Muramyl peptide | T | 0 | α-IFN $10^5$ u | $3 \times 10^5$ u | $10^6$ u | $3 \times 10^6$ u | $6 \times 10^6$ u |
|---|---|---|---|---|---|---|---|
| 0 | | Placebo | control IFN | control IFN | control IFN | control IFN | control IFN |
| | 0 | 6.00 ± 0.80 | 6.03 ± 1.58 | 5.78 ± 2.03 | 3.26 ± 0.85 | 3.22 ± 0.73 | 4.87 ± 2.50 |
| | 24 | 5.50 ± 0.40 | 9.02 ± 2.75 | 10.21 ± 2.20 | 9.20 ± 2.13 | 14.39 ± 2.58 | 20.95 ± 3.73 |
| | 48 | 5.20 ± 0.40 | 9.43 ± 2.11 | 11.20 ± 1.37 | 9.72 ± 2.90 | 14.80 ± 2.22 | 18.73 ± 2.62 |
| MUB 35 μg/Kg | | NT | NT | A II | A III | A IV | A V |
| | 0 | | | 5.23 ± 1.06 | 5.06 ± 0.77 | 4.26 ± 0.34 | 5.21 ± 0.73 |
| | 24 | | | 9.78 ± 1.18 | 13.00 ± 3.62 | 17.31 ± 2.03 | 5.21 ± 3.94 |
| | 48 | | | 10.67 ± 3.41 | 12.41 ± 2.90 | 18.01 ± 3.56 | 21.30 ± 6.25 |
| MUB 100 μg/Kg | | control MUB | A VI | A VII | A VIII | A IX | A X |
| | 0 | 6.37 ± 0.99 | 5.97 ± 1.73 | 4.91 ± 0.96 | 3.83 ± 0.82 | 4.14 ± 0.49 | 5.85 ± 0.68 |
| | 24 | 7.33 ± 0.75 | 11.30 ± 3.64 | 12.43 ± 2.67 | 20.11 ± 6.73 | 19.45 ± 4.09 | 29.14 ± 0.97 |
| | 48 | 8.22 ± 1.39 | 11.76 ± 4.87 | 13.42 ± 2.75 | 18.13 ± 6.92 | 19.18 ± 4.00 | 28.29 ± 0.92 |
| MUM 35 μg/Kg | | NT | NT | NT | B III | B IV | B V |
| | 0 | | | | 4.42 ± 0.70 | 5.67 ± 0.70 | 4.61 ± 1.20 |
| | 24 | | | | 12.48 ± 1.89 | 16.56 ± 1.89 | 21.17 ± 2.37 |
| | 48 | | | | 12.24 ± 2.41 | 14.36 ± 3.47 | 18.33 ± 2.33 |
| MUM 100 μg/Kg | | control MUM | NT | NT | B VI | B VII | B VIII |
| | 0 | 5.43 ± 0.66 | | | 5.20 ± 1.95 | 6.59 ± 162 | 4.06 ± 0.17 |
| | 24 | 7.14 ± 1.00 | | | 16.33 ± 2.13 | 20.78 ± 2.90 | 18.41 ± 2.60 |
| | 48 | 7.39 ± 1.37 | | | 14.49 ± 4.72 | 20.33 ± 4.18 | 16.10 ± 2.74 |

This table shows that, at time 0, all the subjects have normal amounts of neopterine, that the subjects who have received only a placebo have a constant amount of neopterine and that murametide or murabutide at a dose of 100 μg/kg does not influence the amount significantly.

At the lowest doses of interferon, the association with the muramyl peptides enables significant increases in the 5) IL-6 tests:

The test is carried out using an Elisa test kit (British Biotechnology Products Ltd.) on sera taken at time 0 and after 6 hours. The figures express the pg/ml, the normal values are less than 6 pg.

TABLE V

| α-IFN administered | Muramyl peptide administered | | Amounts of IL-6 in the serum |
|---|---|---|---|
| (Number of units) | Compound | dose (μg/Kg) | (Pg/ml)+ |
| 0 | Murabutide | 100 | 2.80 ± 1.60$^S$ |
| 0 | Murabutide | 100 | 4.30 ± 1.80 |
| 1 × 10$^6$ | — | 0 | 2.00 ± 1.70 |
| 1 × 10$^6$ | Murabutide | 100 | 15.00 ± 12.00* |
| 1 × 10$^6$ | Murametide | 100 | 30.00 ± 30.00* |
| 3 × 10$^6$ | — | 0 | 3.60 ± 0.40 |
| 3 × 10$^6$ | Murabutide | 100 | 30.00 ± 23.00* |
| 3 × 10$^6$ | Murametide | 100 | 31.00 ± 19.00 |
| 6 × 10$^6$ | — | 0 | 34.00 ± 56.00 |
| 6 × 10$^6$ | Murabutide | 100 | 76.00 ± 58.00 |
| 6 × 10$^6$ | Murametide | 100 | 107.00 ± 72.00* |

$^{100}$: each group comprised 6 volunteers except for the murametide group which comprised only 4;
+: amounts measured 6 hours after administration; nothing was detected before the administration of the compound detected;
$^S$: mean ± standard deviation;
*: amounts substantially different from the amounts induced by α-IFN alone ($p < 0.05$–$p < 0.005$ in the Mann Whitney Rank test).

Table V shows that murabutide and interferon acted synergistically at all the doses studied.

6) G-CSF tests:

These tests were carried out using the British Biotechnology Products Ltd. kit (see Table VI).

TABLE VI

Amount of G-CSF present in the serum of healthy volunteers before and 6 hours after the administration of the muramyl peptide and α-IFN association

| αIFN administered | Muramyl peptide administered | | Amounts of G-CSF in serum after | |
|---|---|---|---|---|
| (Number of units) | Compound | dose (μg/Kg) | 0 hour | 6 hours |
| 0 | Murabutide | 100 | <10 | 18 ± 9 |
| 0 | Murametide | 100 | 61 ± 103$^X$ | 73 ± 115 |
| 1 × 10$^6$ | — | 0 | <10 | 13 ± 10 |
| 1 × 10$^6$ | Murabutied | 100 | <10 | 58 ± 51$^X$ |
| 1 × 10$^6$ | Murametide | 100 | <10 | 98 ± 81$^X$ |
| 3 × 10$^6$ | — | 0 | <10 | 17 ± 21 |
| 3 × 10$^6$ | Murabutide | 100 | <10 | 77 ± 65 |
| 3 × 10$^6$ | Murametide | 100 | <10 | 79 ± 83 |
| 6 × 10$^6$ | — | 0 | <10 | 17 ± 26 |
| 6 × 10$^6$ | Murabutide | 100 | <10 | 140 ± 168 |
| 6 × 10$^6$ | Murametide | 100 | 12 ± 15 | 284 ± 425$^X$ |

$^+$: each group comprised 6 volunteers except that receiving the murametide which comprised only 4 volunteers;
$^X$: mean ± standard deviation;
*: amounts substantially different from the amounts induced by α-IFN alone ($p < 0.05$–$p < 0.005$ in the Mann Whitney Rank test).

A synergistic activity of the muramyl peptides and the IFN for the induction of G-CSF is observed in this case also.

7) Soluble TNF receptor (STNF-R) tests:

These tests are carried out by an ELISA test in the serum of subjects having 6M units of IFN. At that dose, there is already an appreciable increase in the amount of STNF-R but the addition of murabutide permits a significant increase in the secretion of that mediator.

TABLE VII

| TREATMENT | | Amount of STNF-R in the serum | | |
|---|---|---|---|---|
| α-IFN | Murabutied | (pg/ml) | | Net increase |
| units | (μg/Kg) | 0 hour | 6 hours | (pg/ml) |
| 0 | 100 | 195 ± 28 | 616 ± 65 | 31 ± 37 |
| 6 × 10$^6$ | 0 | 229 ± 37 | 389 ± 95 | 159 ± 108 |
| 6 × 10$^6$ | 100 | 232 ± 35 | 576 ± 139 | 345 ± 120* |

*: significantly different from the amounts induced by α-IFN alone ($p = 0.005$ Mann Whitney Rank test).

8) IL-1, IL-8, α-TNF tests:

The tests were carried out under the same conditions and none of these cytokines was detected in the sera tested. The kits used are all manufactured by British Biotechnology Products Ltd.

9) SECOND SERIES OF TESTS:

9.1. Association of IFN and murabutide:

1) Single administration to humans:

The subjects who had participated in the study were investigated in order to determine the influence of the various treatments on the possible appearance of the following clinical signs: headache, arthralgia-myalgia, fever, shivering, asthenia, nausea-vomiting. A summary of the observations made is given in Table VIII.

TABLE VIII

| | Average frequency and intensity of secondary effects | | | | | |
|---|---|---|---|---|---|---|
| Treatment | Headache | Arthralgia/ myalgia | Fever | Shivering | Asthenia | Nausea |
| α-IFN (6 MU) | 6/6$^a$(1.5)$^b$ | 4/6(1.0) | 6/6(1.2) | 3/6(0.8) | 0/6(0) | 0/6(0) |
| α-IFN (1 MU) + Murabutide (100 μg/kg) | 6/9(1.0) | 5/9(0.8) | 6/9(1.2) | 6/9(1.2) | 1/9(0.1) | 1/9(0.2) |
| α-IFN (6 MU) + Murabutide (100 μg/kg) | 4/6(1.3) | 3/6(0.7) | 6/6(2.3) | 2/6(0.7) | 0/6(0) | 0/6(0) |

TABLE VIII-continued

| | Average frequency and intensity of secondary effects | | | | | |
|---|---|---|---|---|---|---|
| Treatment | Headache | Arthralgia/ myalgia | Fever | Shivering | Asthenia | Nausea |
| α-IFN (1 MU) + Murametide (100 μg/kg) | 4/6(1.0) | 6/6(1.7) | 6/6(1.7) | 3/6(0.8) | 1/6(0.2) | 0/6(0) |
| α-IFN (6 MU) + Murametide (100 μg/kg) | 5/6(1.2) | 4/6(0.8) | 5/6(1.2) | 4/6(1.2) | 3/6(0.7) | 2/6(0.7) |

[a]: number of subjects exhibiting secondary effects compared with the total number of subjects tested
[b]: average intensity of the secondary effects. The score follows the CTC-NCI rules. This score ranges from 0: no secondary effects to 4: effects prohibiting the use of the medicament in the indication considered. Grades 1 and 2 correspond to undesirable but tolerable effects.

This table shows that the secondary effects observed are approximately the same in all the groups. The group which received the 6 MU of IFN alone exhibited a rate of average frequency and intensity of the secondary effects equal to or greater than all the groups associating α-IFN and murabutide; in the case of some of these effects, a reduction in the frequency and intensity of the secondary effects is observed especially in the association IFN (6 MU)+ murabutide.

Table IX shows the biological effects obtained in the same groups, these results indicating that the biological effects obtained by associating murabutide or murametide with α-interferon at 1 MU are at least equal to or are greater than those obtained with α-interferon alone at a dose of 6 MU.

TABLE IX

| | Average of the levels of cytokines induced* | | | |
|---|---|---|---|---|
| Treatment | G-CSF (pg/nl) | IL-6 (pg/nl) | IL-1 RA (ng/ml) | Neutrophil counts in % of the base line Δ |
| α-IFN (6 MU) | 17 ± 26 | 34 ± 56 | 15.5 ± 6.6 | 191 ± 74 |
| α-IFN (1 MU) + Murabutide (100 μg/kg) | 55 ± 56 | 15 ± 12 | 16.1 ± 1.6 | 207 ± 46 |
| α-IFN (6, MU) + Murabutide (100 μg/kg) | 135 ± 166 | 75 ± 59 | 66.9 ± 36.5 | 226 ± 74 |
| α-IFN (1 MU) + Murametide (100 μg/kg) | 94 ± 76 | 30 ± 30 | 16.1 ± 1.8 | 232 ± 78 |
| α-IFN (6 MU) + Murametide (100 μg/kg) | 273 ± 412 | 107 ± 72 | 111 ± 123 | 296 ± 70 |

*: tested 6 hours after injection
Δ: counts carried out from 6 hours to 12 hours after injection These tables therefore show very clearly that the invention makes it possible to benefit from the synergistic effects of the murabutide-cytokine association in the desired effects without increasing the secondary effects. It should be noted that the administration of 1 MU of IFN associated with murabutide or murametide is more active than the administration of 6 MU of IFN alone. In addition, the activity of the 6 MU is increased by the addition of murabutide or murametide, but the secondary effects are reduced.

2) Repeated administration to humans:
Phase I/IIa tests were carried out on 3 groups of 6 healthy volunteers who received the following treatments on days 1, 3 and 5:
a) α-IFN 2a (1 MU) Roferon;
b) murabutide 7 mg c) the association of the two immunostimulants.
These treatments were very well tolerated and, in particular, no appreciable secondary effect was observed in the subjects of group C even after the third injection.

The therapeutic potential of the treatments was evaluated:
a) by investigating the secondary effects:

By studying their influence on the number of circulating neutrophils. The results transcribed in Table X show that the murabutide+IFN association yields a significantly greater increase in the number of neutrophils than that obtained by the immunostimulants administered alone and, interestingly, this phenomenon is as marked after the fifth injection as after the third injection.

TABLE X

| | | Neutrophil count (% of the base line) after: | | |
|---|---|---|---|---|
| Treatment | Day of treatment | 3 hours | 6 hours | 12 hours |
| α-IFN | 1 | 124 ± 27 | 122 ± 30 | 15 ± 20 |
| Murabutide | 1 | 139 ± 26 | 256 ± 51 | 227 ± 46 |
| α-IFN + murabutide | 1 | 112 ± 22 | 187 ± 70 | 156 ± 60 |
| α-IFN | 3 | 121 ± 35 | 126 ± 54 | 151 ± 51 |
| Murabutide | 3 | 133 ± 24 | 182 ± 27 | 176 ± 59 |
| α-IFN + murabutide | 3 | 11E ± 19 | 266 ± 112 | 205 ± 47 |
| α-IFN | 5 | 104 ± 11 | 117 ± 27 | 149 ± 21 |
| Murabutide | 5 | 107 ± 19 | 150 ± 28 | 153 ± 23 |
| α-IFN + murabutide | 5 | 106 ± 11 | 210 ± 103 | 205 ± 56 | b) by analysing the influence of the various treatments on the induction of genes selected for their importance in the manifestation of the biological activity of interferon. These ex vivo experiments were carried out on cells from the circulating blood of the subjects treated.

The products of the following genes: PKR MxA, 2–5 OAS, 9–27 and 15 Kd are the mediators of the antitumour and antiviral activities of IFN, and it is therefore important to verify that murabutide associated with IFN enables levels of induction at least equal to those observed with IFN alone to be obtained.

The analysis of the mRNAs produced by the cells of the subjects of the various groups was carried out by the Northern blot technique and by hybridisation with specific nucleotide probes according to Schreck et al., 1992, Clin. Exp. Immunol. vol. 90, pp. 188–192. This study was carried out on cells taken four hours after treatment, because this is the earliest time at which it is possible to observe the influence of IFN on the induction of the genes sensitive to its action.

The results obtained show that the murabutide-IFN association is at least as active as IFN alone in the activation of the genes concerned.

All of the results obtained in the clinical trials where the murabutide-IFN association was administered three times at two-day intervals show:
- that repeated treatments are as well tolerated as are single administrations;
- that the biological activity of the association manifests itself after the third administration with the same amplitude as after the first, especially as regards the increase in the number of neutrophils and the induction of the genes involved in the antiviral and antitumour activities.

3) In vitro experiments on the influence of the murabutide and α-IFN association on the synthesis of mediators by human monocytes:

Blood taken from healthy volunteers was incubated in vitro with different combinations associating murabutide and α-IFN. The murabutide was used at a dose of 20 μg/ml and the IFN was used at a dose of from 30 to 100 μ/ml. At different times in the course of incubation, blood samples are taken and the mononucleated cells are separated on a Ficoll gradient. The total RNA is extracted, purified and separated by electrophoresis. It is then analysed in accordance with the Schreck method in order to determine by a hybridisation technique what genes were induced by the treatment. This technique demonstrated that very important cytokines are produced by cells under the influence of the murabutide-α-IFN association in addition to cytokines such as IL-1 RA, sTNFR2, IL-6 and G-CSF, the presence of which can be detected in the serum. The results indicated in table XI and obtained in vitro confirm the observations made in the course of the tests (described above) carried out in vivo on healthy volunteers exhibiting the presence of IL-1 RA, sTNFR2, IL-6 and G-CSF in the sera.

Other cytokines, γ-IFN and IL-12, whose role as intercellular mediators is very important, cannot be detected in the circulation but hybridisation techniques demonstrated large amounts of their corresponding RNAs. These cytokines are very involved in defence against intracellular infections.

TABLE XI

| Incubation of the cells | | Average amounts of cytokines secreted | | |
|---|---|---|---|---|
| α-IFN | Murabutide 20 μg/ml | IL-6 pg/ml | sTNFR2 pg/ml | IL-1 RA ng/ml |
| — | − | 1.1 ± 1.6 | 958 ± 290 | 0.3 ± 0.2 |
| — | + | 15.5 ± 11.3 | 1171 ± 478 | 7.8 ± 6.0 |
| 30 u | − | 1.9 ± 1.7 | 1098 ± 222 | 3.5 ± 4.6 |
| 30 u | + | 460.8 ± 330.9 | 1953 ± 483 | 50.8 ± 43.8 |
| 100 u | − | 1.5 ± 0.6 | 1150 ± 286 | 5.0 ± 4.5 |
| 100 u | + | 400.8 ± 313.4 | 1486 ± 625 | 52.0 ± 55.2 |

4) In vivo experiments on Swiss mice demonstrating the activity of the murabutide-IFN association in a toxic shock model:

These experiments demonstrate the effect of the murabutide-IFN association in a toxic shock model and, in particular, a protective effect against endotoxic shock and a synergistic activity with interferon.

The administration of D-galactosamine with lipopolysaccharide (LPS) to Swiss mice induces endotoxic shock with at least 70% mortality in 24–48 hours. The prophylactic or therapeutic effect of murabutide was studied in this model in order to evaluate its anti-inflammatory activity when it is administered alone or in combination with α/β-IFN. The pretreatment of the mice with murabutide or with α/β-interferon does not give rise to a prophylactic effect with respect to a contest with the galactosamine/LPS mixture (Table XII). On the contrary, pretreatment with a combination of murabutide and α/β-interferon induces significant protection with an incidence of mortality of only 33% (against 78% in the controls).

The administration of murabutide to the mice 1 hour after the induction of endotoxic shock has a significant curative effect which is far superior to that induced by the administration of α/β-interferon. On the other hand, the treatment with a combination of murabutide and α/β-interferon demonstrates a highly synergistic therapeutic activity with approximately 80% protection of the mice against mortality due to endotoxic shock.

TABLE XII

Protection against endotoxic shock in a galactosamine mouse model, by prophylactic or therapeutic administration of murabutide with murine α/β-interferon[1].

| Treatment | | | Number of dead mice per total tested | | | Average % mortality |
|---|---|---|---|---|---|---|
| Compound [2] | Dose | Time | Exp. 1 | Exp. 2 | Exp. 3 | |
| NaCl | — | −3 hrs | 6/9 | 7/8 | 8/10 | 78 |
| Murabutide | 15 mg/kg | −3 hrs | 7/9 | 7/8 | 6/10 | 74 |
| α/β-IFN | 5 × 10$^5$ IU/kg | −3 hrs | 8/9 | 5/8 | 9/10 | 81 |
| α/β-IFN + Murabutide | 5 × 10$^5$ U/kg + 15 mg/kg | −3 hrs | 7/9 | 5/8 | 5/10 | 63 |
| α/β-IFN | 1.25 × 10$^6$ IU/kg | −3 hrs | 7/9 | 8/8 | 6/10 | 78 |
| α/β-IFN + Murabutide | 1.25 × 10$^6$ IU/kg + 15 mg/kg | −3 hrs | 1/9 | 4/8 | 4/10 | 33 |
| NaCl | — | +1 hr | 6/9 | 7/8 | 6/9 | 73 |
| Murabutide | 15 mg/kg | +1 hr | 2/9 | 3/8 | 3/9 | 31 |
| α/β-IFN | 11.25 × 10$^6$ IU/kg | +1 hr | 6/9 | 3/8 | 6/9 | 58 |
| α/β-IFN + Murabutide | 1.25 × 10$^6$ IU/kg + 15 mg/kg | +1 hr | 1/9 | 1/8 | 1/9 | 12 |

[1] The Swiss mice were tested intraperitoneally at time 0 with 18 mg of D-galactosamine + 50 ng of LPS. The mortality was measured after 48 hours.
[2] The compounds are administered intravenously either 3 hours before or 1 hour after the test.

The results clearly show that the combination of α/β-interferon+murabutide results in a drastic reduction in the mortality of the mice tested with D-galactosamine and LPS, whether prophylactically (33% mortality against 75% to 81% in the absence of this composition) and 12% mortality therapeutically against 30% to 73% in the absence of the combination of α/β-IFN+murabutide.

9.2. Association with GM-CSF:

Studies similar to those described above were carried out in order to study the murabutide-GM-CSF association. These studies were carried out in vitro on the cells of healthy volunteers after incubation with immunomodulators alone or in association.

a) RNA analysis:

An induction of the synthesis of the interferon receptor and of the synthesis of IL-1 RA was observed in all the donors tested.

b) Analysis of the supernatants:

Specific cytokines were sought and measured in the supernatants (see Table XIII). This analysis confirms that large amounts of IL-1 RA are produced under the influence of the association, indicating that murabutide should permit better tolerance of GM-CSF, some of the secondary effects of which are associated with inflammatory phenomena.

The results obtained in these experiments therefore indicate that, as in the case of IFN, the murabutide-GM-CSF association permits substantial induction of mediators not appearing during separate treatments. In addition, the induction of these mediators indicates that murabutide must increase tolerance to the administration of GM-CSF.

TABLE XIII

| Incubation of the cells | | Average amounts of cytokines secreted | | |
|---|---|---|---|---|
| Cytokine (ng/ml) | Murabutide 20 μg/ml | IL-6 pg/ml | sTNFR2 pg/ml | IL-1 RA ng/ml |
| — | − | 1.1 ± 1.6 | 958 ± 290 | 0.3 ± 0.2 |
| — | + | 15.5 ± 11.3 | 1171 ± 478 | 7.8 ± 6.0 |
| GM-CSF(1) | − | 2.0 ± 1.5 | 1027 ± 624 | 4.0 ± 1.4 |
| GM-CSF(1) | + | 34.8 ± 25.2 | 1396 ± 341 | 57.1 ± 26.9 |
| GM-CSF(5) | − | 2.3 ± 2.1 | 1359 ± 350 | 8.7 ± 10.0 |
| GM-CSF(5) | + | 52.8 ± 70.9 | 1970 ± 545 | 76.3 ± 47.0 |

9.3. Association with IL-2:

1) In vivo experiment on mice using murametide:

IL-2 has been found to have important therapeutic effects in cases of metastatic renal carcinomas and malignant melanomas. Its use is nevertheless limited by its very substantial toxic effects which produce a syndrome resembling toxic shock which may be lethal in 25% of cases.

A murine model has been developed in C3H/HeN mice. KHT sarcoma cells are administered by the venous route. After 4 days and 6 days they are treated with:

a) murametide alone;
b) IL-2;
c) the association of the two immunomodulators;
d) a fourth group is not treated.

Murametide in combination with interleukin-2 as immunotherapy treatment for cancers which have spread:

Immunotherapy with IL-2 has been found to be efficacious in the treatment of metastatic carcinomas of renal cells and of malignant melanomas. Despite its efficacy, the administration of IL-2 is accompanied by a series of secondary effects of the septic type which have limited the administrable doses and meant that it can be used in specialised medical centers only. When it is administered with IL-2, the adjuvant peptide of murametide reduces the toxicity of IL-2 in mice having tumours. Mice receiving IL-2 alone congregate together and are generally inactive. In survival studies, mice receiving the combination of IL-2 and murametide survive those receiving IL-2 alone. Although murametide alone has no antitumour activity in mice having pulmonary sarcoma metastases, the combination of IL-2 and murametide is more effective than IL-2 alone. These preliminary data suggest that murametide can be used in combination with IL-2 as a means of reducing the toxicity of strong doses of IL-2 treatment.

2) In vitro experiments on human cells using murabutide:

In experiments carried out on cells of healthy volunteers, it has been shown that the association of IL-2 with murabutide enables a very large amount of RNA coding for γ-IFN and IL-12 to be obtained. These two cytokines are essential for antitumour activity. It should be noted that there is no synthesis of TNF, the production of which during treatments with IL-2 is responsible for a large proportion of the secondary effects, especially cachexia.

All of the in vivo and in vitro results obtained indicate clearly that the association of murabutide with IL-2 must permit a better therapeutic effect with fewer secondary effects both because lower doses of IL-2 are necessary and because murametide or murabutide reduces the toxic effects of IL-2.

The results obtained therefore demonstrate the following:

A) Especially in respect of interferon:

a) At doses at which it is incapable of significantly modifying the rate of neopterine synthesis when it is administered alone, the association of α-IFN with murabutide or murametide enables large amounts of this marker to be obtained. At higher doses of IFN, the association permits a significant increase in its amount. Since neopterine is considered to be one of the principal markers of the activity of interferon in respect of human macrophages, these results show that α-IFN effects associated with the activation of these cells can be obtained with reduced doses, which are well tolerated; a similar comment applies to IL-1 RA, extremely large amounts of which are observed after the administration of the association. It is even observed that there is a synergistic activity between IFN and murabutide or murametide and that a dose-effect is obtained because the amount of IL-1 RA is approximately doubled when the dose of IFN is doubled. The same observation may be made with regard to STNF-R which is induced by IFN alone but only slightly in comparison with the amounts induced by the association.

b) The association of IFN with the muramyl peptide enables higher leucocyte counts to be obtained compared with those of the controls;

c) The association of the muramyl peptides with α-IFN also brought about the selective secretion of other cytokines or immunity mediators. It is noted in the subjects treated with the association that there are significant differences between the amount of IL-6, G-CSF and STNF-R in their serum and that of subjects treated with IFN alone or murabutide alone. On the other hand, there appears to be no increase in the amount of IL-1, IL-8 or α-TNF. This selective effect of the association of muramyl peptides with interferon on the secretion of cytokines is quite unexpected and is of particular value. It could not have been foreseen from the known properties of the two components administered alone. This finding offers very valuable possibilities of application.

B) G-CSF is the cytokine responsible for the differentiation of basal cells towards the granulocyte line and for their regeneration after a myelotoxic and IL-6 treatment and is also greatly involved in haematopoiesis. Thus, the possibility of associating with the activity of exogenous α- IFN the activities of endogenbus G-CSF and IL-6 induced by that exogenous α-IFN administered to the host constitutes an important therapeutic advance:
  a) this association is effected under conditions of minimum secondary effects; the doses of IFN required are not very high;
  b) it occurs under much more physiological conditions of dosage and availability than if a cocktail of the corresponding cytokines were administered;
  c) the absence of secretion of TNF, IL-1 and IL-8 is a particularly favourable element, all the more so because STNF-R is secreted which, combining with any TNF, would neutralise its action as would IL-1 RA if there were an active quantity of IL-1. All these data lead to new therapeutic applications in human medicine and to a widening of the existing fields of therapeutic application. In particular:
    1. all situations where the therapeutic value of α-IFN can henceforth be demonstrated. In particular, the invention permits the extension of interferons in this form of association to treatments of tumour disorders which are hardly contemplated at present, basically because of the excessive relative importance of the secondary effects examined above. Kaposi's sarcoma, chronic myeloidal leukaemia, various carcinomas, multiple myeloma, melanoma, various leukaemias and lymphomas may be mentioned. Owing to the stimulant effect exerted in respect of the production of therapeutically useful cytokines, the invention permits the reconstitution of at least some of the complex biological physiological systems normally involved in the maintenance of homoeostasis, owing to the interaction of their constituents with other regulation factors which are soluble or associated with the cells.
    2. more especially, situations involving a deficit of the granulocyte lines which is spontaneous, as in the case of myelodysplastic syndromes, or which is induced by medical treatments, especially treatments based on cytokines. One of the great advantages of using the association according to the invention resides in the protection of the host against the leucopenic action of the same cytokines used alone, so that cytotoxic compounds using the appropriate cytokine, especially for the treatment of cancers, infectious diseases or deficiencies of genetic origin, can be prolonged until a more reliable curative effect is permitted. In other words, the association permits either a slowing-down of the depletion, or even sufficient restoration, of the granulocyte system (or even a repair of the marrow) each time the latter is affected by a cytotoxic treatment (cancer radiotherapy or chemotherapy, treatment of AIDS by AZT) and/or by an immunosuppressant treatment. An association can also be used in situations according to the invention (cytokine and muramyl peptide) where the cytotoxic agents used differ from the cytokine of the association, concurrently with the cytotoxic treatment of the type in question, or each time the treatment with the cytotoxic agent is interrupted in order to permit restoration of the phagocytes and of the blood platelets and stimulation of the bone marrow. Finally, the invention opens up the way to a more rapid reconstitution of the haematopoietic system in persons whose immune system has previously been inhibited or even destroyed, for example in order to permit the transplanting of bone marrow or, more generally, of allogenic organs or tissues.

The induction of IL-6 would also lead to the belief that the association has an effect o n megacharyocytopoiesis and therefore on the regeneration of platelets. This was also observed in some of the subjects who were monitored over two weeks.

Within the framework of this anti-neutropenic or antileucopenic effect, the invention relates also to compositions comprising an association of a cytokine, for example interferon or an interleukin, associated, on the one hand, with GM-CSF and, on the other hand, with a muramyl peptide and especially a murabutide; as has been seen, cytokine has the therapeutic effect in humans of reducing tumours or a viral infection, but among all these secondary effects it confers on the patient a very harmful neutropenia or leucopenia.

As regards GM-CSF, when it is administered alone it confers on patients very great secondary effects of the inflammatory type, but it also has an antineutropenic or antileucopenic effect as a result of increasing the number of neutrophils and leucophils in the blood; it has been seen that muramyl peptide, such as murabutide or murametide, also repairs the neutropenic or leucopenic effect of cytokines.

The association of GM-CSF, a cytokine, for example interferon or IL-2, and muramyl peptide is therefore an association of three products: the murabutide and the GM-CSF having a cumulative repairing effect on neutropenia and enabling the secondary effects of GM-CSF alone to be eliminated.

C) A substantial production of IL-1 RA and of STNF-R is also observed with no secretion of TNF, IL-1 and IL-8. This gives rise to a second range of applications. First of all towards the prevention and treatment of septic shock in which IL-1 and TNF play a fundamental part. The other indications are all those where it is necessary to oppose inflammation, as in the case of rheumatoid arthritis or certain auto-immune diseases or diseases induced in the case of marrow, tissue or organ transplantation as a result of a reaction of the transplanted organ against the host.
  D) The association can of course also be used in the treatment of viral diseases, such as chronic hepatitis C or B or respiratory viral infections, regardless of whether the treatment concerned is one in which the cytokine is directly involved in its antiviral capacity (for example in the case of interferon) or one which is a substitute treatment or a treatment interposed between antiviral treatments that have to be interrupted intermittently (for example, inhibition of the viral multiplication of HIV by AZT or other nucleoside derivatives having a similar spectrum of antiviral action).

In general, therefore, the invention relates to any association satisfying the above-mentioned criteria and also containing, where appropriate, a pharmaceutically acceptable carrier. Without implying any limitation, these pharmaceutical compositions are advantageously formed by solutions which can be administered parenterally, especially subcutaneously, intravenously, or by perfusion. The muramyl peptides can be administered orally either alone or in a galenical form ensuring their protection (for example encapsulated in capsule or microsphere liposomes enabling the gastric barrier to be crossed). The same applies to the cytokines used, especially the interferons.

In the case of the interferon and muramyl peptide association, the preferred doses of IFN for injection are of the order of $5\times10^4$ to $5\times10^6$ (0.05M to 5M) International Units and the doses of muramyl peptide, especially murametide or murabutide, are of the order of from 10 µg to 250 µg/kg.

In the case of the associations of GM-CSF and muramyl peptides, preferred doses are, respectively, from 1 to 25 µg/kg of GM-CSF for from 10 µg to 250 µg/kg of muramyl peptides.

It will be appreciated that the doses indicated above have no other value than that of illustrating the invention. It will of course be up to the practitioner to determine what doses of the constituents of the association are to be associated, according to the condition of the patient and the disorder from which he/she is suffering.

The invention relates also to the association with IL-2 which exhibits recognised antitumour activities, in particular with regard to metastases of renal carcinoma or other cancers, but the therapeutic index of which is extremely weak. The preferred doses for injection are from 1 to 10 million units kg/day of IL-2 associated with from 10 µg to 250 µg/kg of muramyl peptides.

By way of supplementary examples, the invention relates also to associations with a muramyl peptide of the type indicated, of IL-6, γ-IFN and/or TGF-β factor (transforming growth factor). They are believed to be greatly involved in the negative regulation of class IgE immunoglobulins which are responsible for allergic phenomena. "Negative regulation" is to be understood as meaning a reduction in the production of class IgE immunoglobulins relative to the production of other immunoglobulins, especially IgA and IgG immunoglobulins. The administration of the association of one or more of these cytokines associated with a muramyl peptide enables the profile of the immunoglobulins synthesised by the cells of the immune system to be modulated, in a direction promoting the production of IgG and IgA rather than IgEs, and even to the detriment of the latter. This result demonstrates the possibility of using the association according to the invention in the therapeutic treatment of allergies.

The doses of each of the constituents of the association, especially when they are administered parenterally, are especially the following, for approximately from 10 µg to 250 µg/kg of muramyl peptide:

from 0.05 M to 10 M IU of γ-IFN/kg and per day, preferably from 0.5 M IU/kg/day to 5 M IU/kg/day and more preferably from 1 M IU/kg/day to 5 M IU/kg/day;
from 0.5 µg to 100 µg/kg of TGF-β; and/or
from 0.1 µg to 25 µg/kg of IL-6.

Finally, it will be appreciated that the following claims can extend their effects only to compositions which involve, in association with the chosen cytokine, a molecule of the muramyl peptide type that can be used in human therapeutics or a molecule that exhibits the essential biological properties of that muramyl peptide. The following products may be mentioned by way of example:

Nac Mur-L-Thr-D isoGln-sn glyceryl dipalmitoyl
NAc-Mur-L-Ala-D-isoGln-L-Ala-2 (1',2'-dipalmitoyl)-sn-glycero-3'-phosphorylethylamide (MTP-PE);
$N_2$ (Nac-Mur-L-Ala-D-isoGln) $N_6$-stearoyl-L-Lysine (Muroctasine) or MDP-Lys (L18)
NAc-glucosaminyl-NAc-Mur-L-Ala-D-isoGln-L-Ala-glyceryl-dipalmitate (DTP-GDP) or NAc-glucosaminyl-NAc Mur-L-Thr-D-iso-Gln-L-Ala-glyceryl-dipalmitate
Nac-Mur-L-Thr-D-isoGln;
Nac-Mur-D-Ala-D-isoGln-1,2-dipalmitoyl-sn-glycerol
Nac-Mur-D-Thr-D-isoGln-1,2-dipalmitoyl-sn-glycerol
Analogues of MDP in which the second amino acid, glutamine, has been replaced by a norleucine and which are devoid of pyrogenic activity;
Derivatives or analogues (obtained by fractionation or, better, by synthesis) of bacterial products sufficiently devoid of toxicity, especially pyrogenicity, including endotoxins, especially monomers or peptidoglycan endotoxins, capable of activating the immunologically competent cells and of inducing cytokines in humans.

We claim:

1. A therapeutic composition association which comprises at least one natural or recombinant cytokine selected from the group consisting of an interferon, an CSF and an interleukin, and at least one hydrophilic muramyl peptide having the following formula:

wherein the group R is a methyl group;
X is L-alanyl or L-threonyl;
$R_7$ is an $O(CH_2)_{x'}H$ group, wherein X'=1, 2, 3 or 4; and
$R_8$ is an amino group or an $O(CH_2)_{x''}H$ group, wherein x''=1, 2, 3 or 4.

2. The composition according to claim 1, wherein said muramyl peptide also induces in vivo an increased synthesis of IL-6 or G-CSF or both.

3. The composition according to claim 1, wherein
$R=CH_3$,
X is L-alanyl,
$R^7$ is an $O(CH_2)_{x'}H$ group, wherein x'=1, 2, 3 or 4, and
$R^8$ is an amino group or an $O(CH_2)_{x''}H$ group, wherein x''=1, 2, 3 or 4.

4. The composition according to claim 1, wherein the muramyl peptide is selected from the group consisting of, murametide, murabutide, muradimetide and homologues thereof wherein an L-threonyl residue is substituted for the L-alanyl residue of muramyl peptide group.

5. The composition according to claim 1, wherein said cytokine is β-interferon.

6. The composition according to claim 2, wherein said cytokine is β-interferon.

7. The composition according to claim 1, wherein said cytokine is interleukine 2.

8. The composition according to claim 2, wherein said cytokine is interleukine 2.

9. The composition according to claim 1, wherein said CSF is GM-CSF.

10. The composition according to claim 2, wherein said CSF is GM-CSF.

11. The composition according to claim 4, wherein said cytokine is interleukine 2.

12. The composition according to claim 1, wherein $R^7$ is $OC_4H_9$ or —O—$CH_3$ and $R^8$ is —$NH_2$ or —O—-$CH_3$.

13. The composition according to claim 1, wherein $R^7$ is $OC_4H_9$ or —O—$CH_3$ and $R^8$ is —$NH_2$.

14. The composition according to claim 13, wherein said cytokine is β-interferon or GM-CSF.

15. The composition according to claim 1, wherein $R^7$ is $OCH_3$ and $R^8$ is —$OCH_3$.

16. A method for the treatment of a patient with a cytokine selected from the group consisting of an interferon, a CSF and an interleukin, which comprises co-administering said cytokine, close in time, with a hydrophilic muramyl peptide of claim 1.

17. A method for the treatment of cancers, infections, diseases or genetic deficiencies, which comprises co-administering a cytokine selected from the group consisting of an interferon, a CSF and an interleukin, close in time, with a hydrophilic muramyl peptide of claim 1.

18. A method for inducing the granulocyte system in a patient, which comprises co-administering a cytokine selected from the group consisting of an interferon, a CSF and an interleukin, close in time, with a hydrophilic muramyl peptide of claim 1.

19. A method for promoting a rapid reconstitution of the haematopoietic system in a patient whose immune system has been inhibited, which comprises co-administering a cytokine selected from the group consisting of an interferon, a CSF and an interleukin, close in time, with a hydrophilic muramyl peptide of claim 1.

20. A method for the treatment of viral diseases, which comprises co-administering a cytokine selected from the group consisting of an interferon, a CSF and an interleukin, close in time, with a hydrophilic muramyl peptide of claim 1.

21. A method for the prevention or treatment of septic shock, which comprises co-administering cytokine selected from the group consisting of an interferon, a CSF and an interleukin, close in time, with a hydrophilic muramyl peptide of claim 1.

22. A method for the treatment or prevention of the inflammatory processes, which comprises co-administering a cytokine selected from the group consisting of an interferon, a CSF and an interleukin, close in time, with a hydrophilic muramyl peptide of claim 1.

23. The method according to any one of claims 16–22, wherein said cytokine is GM-CSF or IL-2.

24. The method according to any one of claims 16–22, wherein said muramyl peptide is administered in an amount of 10 to 350 ug/kg/day.

25. The method according to claim 24, wherein said muramyl peptide is administered in an amount of 50 to 200 ug/kg/day.

26. The method according to any one of claims 16–22, wherein said muramyl peptide is administered in an amount of 50 to 200 ug/kg/day.

27. The method according to claim 26, wherein said cytokine is interferon and is administered in an amount of 0.05 to 5 MU/kg/day.

28. The method according to claim 26, wherein said cytokine is IL-2 and is administered in an amount of 0.3 to 2 MU/kg/day.

29. The method according to claim 26, wherein said cytokine is GM-CSF and is administered in an amount of 5 to 10 µg/kg/day.

30. The composition according to claim 1, wherein said cytokine is α-interferon.

* * * * *

UNITED STATES PATENT AND TRADEMARK OFFICE
CERTIFICATE OF CORRECTION

PATENT NO. : 5,932,208                  Page 1 of 3
DATED       : August 3, 1999
INVENTOR(S) : Chedid et al.

It is certified that error appears in the above-identified patent and that said Letters Patent is hereby corrected as shown below:

In column 4, starting at line 31, the lower part of the formula presenting the glutamine residue should be corrected to read:

-- 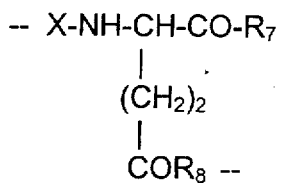 --

Rather than

"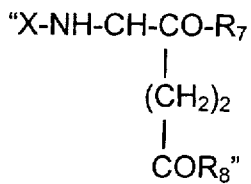"

UNITED STATES PATENT AND TRADEMARK OFFICE
CERTIFICATE OF CORRECTION

PATENT NO. : 5,932,208
DATED : August 3, 1999
INVENTOR(S) : Chedid et al.

It is certified that error appears in the above-identified patent and that said Letters Patent is hereby corrected as shown below:

In column 9, Table VI, under the last vertical column (heading: 6 hours), the symbol "X" after the values 51, 81 and 425 should be replaced by the symbol --*--.

In column 15, line 15, please correct "interferon receptor" to read --interferon-γ receptor --.

UNITED STATES PATENT AND TRADEMARK OFFICE
CERTIFICATE OF CORRECTION

PATENT NO. : 5,932,208
DATED : August 3, 1999
INVENTOR(S) : Chedid et al.

It is certified that error appears in the above-identified patent and that said Letters Patent is hereby corrected as shown below:

In column 19, line 66 to column 20, line 2, please change

"glyceryl-dipalmitate (DTP-GDP) or NAc-glucosaminyl-

NAc

Mur-L-Thr-D-iso-Gln-L-Ala-glyceryl-dipalmitate

NAc-Mur-L-Thr-D-isoGln;"

to properly read:
-- glyceryl-dipalmitate (DTP-GDP) or NAc-glucosaminyl-

NAc Mur-L-Thr-D-iso-Gln-L-Ala-glyceryl-dipalmitate; --

Signed and Sealed this

Twenty-eighth Day of November, 2000

Attest:

Q. TODD DICKINSON

*Attesting Officer*   *Director of Patents and Trademarks*